United States Patent [19]

Kimura et al.

[11] Patent Number: 5,036,098
[45] Date of Patent: Jul. 30, 1991

[54] BUTYNYLAMINE DERIVATIVES AND THEIR PRODUCTION

[75] Inventors: Kiyoshi Kimura, Takatsuki; Masahiro Kise; Iwao Morita, both of Kyoto, all of Japan

[73] Assignee: Nippon Shinyaku Co., Ltd., Japan

[21] Appl. No.: 407,228

[22] Filed: Sep. 14, 1989

[30] Foreign Application Priority Data

Sep. 14, 1988 [JP] Japan ................... 63-231272

[51] Int. Cl.⁵ ............... C07C 69/732; C07D 333/22; A61K 31/215; A61K 31/38
[52] U.S. Cl. ..................... 514/438; 514/444; 514/529; 514/530; 514/534; 544/59; 544/168; 544/171; 544/397; 546/234; 546/239; 548/568; 548/572; 549/59; 549/77; 560/58; 560/118; 564/171; 564/188
[58] Field of Search ............ 560/58, 118; 549/59, 549/77; 514/438, 444, 529, 530, 534

[56] References Cited
FOREIGN PATENT DOCUMENTS 62-267224 11/1987 Japan .

OTHER PUBLICATIONS

The Merck Index, 11th ed. (1989), Budavari (editor), p. 1100, Merck and Co., Inc.
Carol S. Weil, "Tables for Convenient Calculation of Median Effective Dose ($LD_{50}$ OR–$ED_{50}$) And Instructions in Their Use", *Biometrics*, 8, 249–253 (1952).

*Primary Examiner*—Mukund J. Shah
*Assistant Examiner*—Philip Datlow
*Attorney, Agent, or Firm*—Rosenman & Colin

[57] ABSTRACT

Compounds of the formula (I):

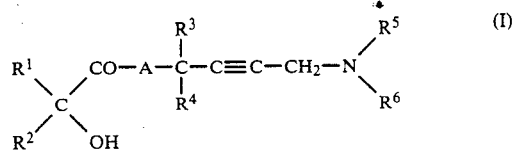

exhibit anti-cholingeric and calcium antagonistic action and are used for treating pollakiuria and incontinence in humans and animals.

21 Claims, No Drawings

BUTYNYLAMINE DERIVATIVES AND THEIR PRODUCTION

The present invention is concerned with butynylamine derivatives and their production, pharmaceutical compositions containing those compounds as the active therapeutic agent and to methods of treating pollakiuria and other hyperactive bladder conditions as well as urinary incontinence which comprises administrating to a human or animal in need thereof an effective amount of such a compound.

According to the prior art, flavoxate has been generally used as a treatment for pollakiuria. Terodiline and oxybutynin have recently been marketed following flavoxate. Of these compounds oxybutynin is similar to the compounds of the present invention in structure, but exhibits side effects such as thirst because of the too pronounced anti-cholinergic action thus providing serious disadvantages for administration to humans and animals.

The present invention is directed to achieving compounds which provide a useful treatment for pollakiuria but are free from the disadvantages of the prior art compounds.

More particularly, the present invention is concerned with butynylamines of the formula (I):

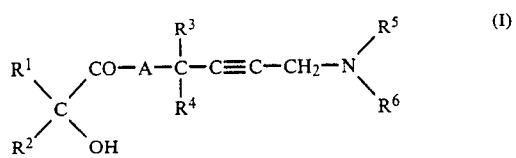

or a pharmaceutically acceptable acid addition salt thereof, wherein $R^1$ and $R^2$ are the same or different and each is cycloalkyl of 5 to 7 carbon atoms, phenyl or 2-thienyl; $R^3$, and $R^4$ are the same or different and each is hydrogen or straight or branch chain lower alkyl, or $R^3$ and $R^4$ together with the carbon atom to which they are attached are cycloalkyl of 5 to 6 carbon atoms; $R^5$ and $R^6$ are the same or different and each is hydrogen or straight or branch chain lower alkyl, or $R^5$ and $R^6$ together with the nitrogen atom to which they are attached are cyclic amino or cyclic amino having an oxygen, sulphur or nitrogen atom as a second heteroatom, said cyclic amino being unsubstituted or substituted by lower alkoxyphenyl; and A is 0 or NR wherein R is hydrogen or straight or branch chain lower alkyl, provided that when either $R^1$ or $R^2$ is phenyl and $R^3$ and $R^4$ are both hydrogen, A is not 0.

In formula (I), the cycloalkyl moiety of $R^1$ and $R^2$ is cyclopentyl, cyclohexyl or cycloheptyl.

The alkyl moiety of $R^3$ and $R^4$ is preferably methyl, ethyl, n-propyl, isopropyl, n-butyl, isobutyl, sec-butyl and tertbutyl.

Preferably, $R^3$ and $R^4$ are the same or different and each is hydrogen or straight or branch chain alkyl of 1 to 4 carbon atoms, or $R^3$ and $R^4$. together with the carbon atom to which they are attached are cycloalkyl of 5 or 6 carbon atoms.

$R^5$ and $R^6$ are the same or different and each is hydrogen or straight or branch chain alkyl preferably of 1 to 4 carbon atoms.

$R^5$ and $R^6$ together with the nitrogen atom to which they are attached are cyclic amino or cyclic amino having an oxygen, sulphur or nitrogen atom as a second heteroatom, the cyclic amino being unsubstituted or substituted by alkoxyphenyl wherein the alkoxy moiety is straight or branch chain preferably of 1 to 4 carbon atoms.

The cyclic amino moiety preferably is pyrrolidino, piperidino, piperazino, morpholino, thiomorpholino or homopiperazino, unsubstituted or substituted by methoxyphenyl, ethoxyphenyl, n-propoxyphenyl, isopropoxyphenyl, n-butoxyphenyl, isobutoxyphenyl, sec-butoxyphenyl or tert-butoxyphenyl.

According to one embodiment of the present invention A is 0.

When A is NR wherein R is hydrogen or straight or branch chain alkyl preferably of 1 to 4 carbon atoms.

When the cyclic amino moiety also has an alkoxyphenyl moiety as a substituent, the alkoxy moiety preferably is methoxy, ethoxy, n-propoxy, isopropoxy, n-butoxy, isobutoxy, sec-butoxy or tert-butoxy.

Pharmaceutically acceptable acid addition salts according to the present invention include those with mineral acids such as hydrochloric acid, sulfuric acid, nitric acid and phosphoric acid as well as those with organic acids such as oxalic acid, tartaric acid, maleic acid and benzenesulfonic acid.

The compounds of this invention may be prepared, for example, by the following methods.

Method A

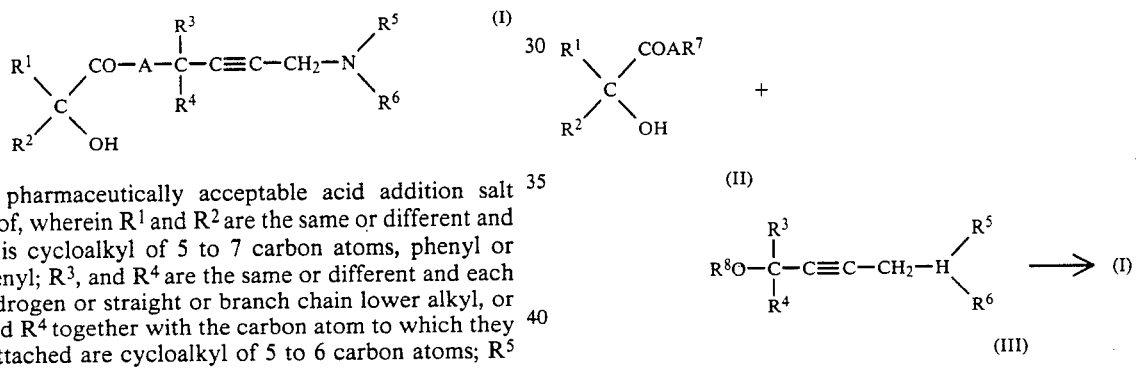

wherein A and $R^1$ through $R^6$ are as above defined; $R^7$ is lower alkyl; and $R^8$ is hydrogen or lower alkanoyl.

Compounds of formula (I) can be prepared by reaction between an ester or amide of formula (II) and a 2-butyne compound of formula (III) by a method per se known.

For example, the reaction is carried out in an inert solvent in the presence of a base catalyst (e.g., potassium or sodium alkoxides) while removing the formed alcohol from the reaction system through a dehydration tube. When R. is methyl, in particular, use of molecular sieves to selectively adsorb the formed methanol gives a high yield of compound (I). As the reaction medium, any solvents commonly employed in this type of reaction may be used, such as hydrocarbons (e.g., benzene, toluene, n-pentane, n-hexane and petroleum ether), ethers (e.g., anhydrous diethyl ether, tetrahydrofuran, isopropyl ether, dioxane, dimethoxyethane, diethylene glycol and dimethyl ether), and aprotic solvents (e.g., acetonitrile, N,N-dimethylformamide and sulfolane). The reaction temperature is in the range from 50° to 200° C., preferably from 90° to 120° C. The amount of compound (III) to be used is 1 to 2 molar proportions, preferably 1 to 1.2 molar proportions, based on the weight of compound (II).

A high yield of compound (I) can also be obtained by the use of an acid catalyst (e.g., sulfuric and p-toluenesulfonic acids), if compound (III) is used in large excess, or a methyl ester is used as compound (II) to effectively remove the lowboiling methanol thus formed.

Method B (Grignard reaction)

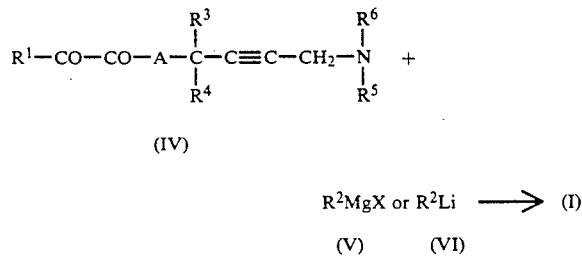

wherein A and $R^1$ through $R^6$ are as above defined.

Compounds (I) may be prepared by reaction of a compound (IV) with a Grignard reagent (V) or a lithium compound (VI). The reaction is carried out in an inert solvent at a temperature in the range from $-78°$ to $100°$ C., preferably from $-20°$ to $50°$ C. The most preferred reaction medium is an ether solvent, such as anhydrous diethyl ether, tetrahydrofuran, isopropyl ether, dioxane, dimethoxyethane, diethylene glycol and dimethyl ether, but a hydrocarbon (e.g., benzene, toluene, n-pentane, n-haxane and petroleum ether) or an amine (in some cases) may also be used as solvent. The reaction is generally carried out by dissolving 1.0 to 0.8 equivalent proportion of a compound (IV) in a small volume of solvent and adding a Grignard reagent or a lithium compound to this solution.

Method C (Mannich reaction)

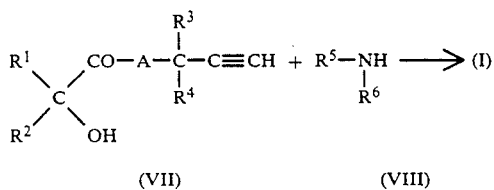

wherein A and $R^1$ through $R^6$ are as above defined.

Compounds (I) may also be prepared by Mannich reaction from a compound (VII) and a secondary amine (VIII), which is carried out in the presence of an aldehyde in a solvent inert to the reaction or without using any solvent. As the reaction medium, any solvents commonly employed in this type of reaction may be used, such as alcohols (e.g., methanol, ethanol, propanol and butanol), ethers (e.g., tetrahydrofuran and dioxane), aprotic solvents (e.g., acetonitrile, N,N-dimethylforamide, dimethyl sulfoxide and sulfolane), water, and mixtures thereof. As the aldehyde, any compounds showing action equivalent to formaldehyde in Mannich reaction may be used, such as paraformaldehyde, formalin, methylal, ethylal, piperidinomethylphthalimide and hexamethylenetetramine. The suitable amounts of aldehyde and secondary amine to be used are 1 to 10 molar proportions based on the weight of compound (VII). The secondary amine may also be used in the form of a salt. A catalytic amount (0.01 to 0.1 molar proportion) of zinc chloride or a copper salt (e.g., cuprous chloride and acetate) may be added to the reaction system to accelerate the reaction. The reaction should normally be carried out at a temperature in the range from 0 to $100°$ C. The suitable reaction time may vary with the types of reactants and aldehyde used, the reaction temperature and other factors, but is normally in the range from 20 minutes to 40 hours.

Method D

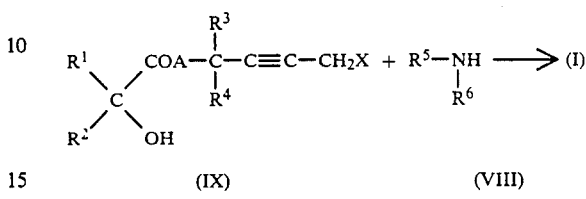

wherein A and $R^1$-$R^6$ are as above defined and X is halogen.

A compound of formula (I) is reacted with an amine of the formula (VIII) to produce a compound of the formula (I). The reaction is carried out in an inert solvent usually at $-20°$ to $+100°$ C. With respect to the solvent, those which are commonly used in the reaction of this kind may be used, for example, ethers (e.g. tetrahydrofuran, dioxane, ether, etc.) and aromatic hydrocarbons (e.g. benzene, toluene, etc.). The amount of the amine (VIII) is in a substantial excess (preferably 5 to 10 times as much moles) to (IX).

Starting materials represented by the formulas (III), (IV) and (VII) include novel compounds, which can be prepared by the known methods [J. Org. Chem., 27, 2905 (1962); J. Am. Chem. Soc., 71, 3722 (1949); J. Med. Chem., 13, 1249 (1970); Acta. Pharm. Suecica, 6, 349 (1969); B.P. 1051723; U.S. Pat. No. 3202655] or according to the methods described in the Reference Examples below.

The compounds (I) thus formed can be isolated and purified in the form of the free base or as an acid addition salt by known techniques, such as concentration, pH adjustment, extraction, crystallization, fractional distillation and chromatography.

When the compounds of the present invention are administered as pharmaceuticals, to humans and animals, they are given per se or as a pharmaceutical composition containing, for example, 0.1 to 99.5% (more preferably, 0.5 to 90%) of active ingredient in combination with a pharmaceutically acceptable carrier.

The compounds of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

As to carriers, one or more liquid, solid or semisolid diluent, filler and other auxiliary agents for pharmaceutical preparations may be used. It is desired that the pharmaceutical compositions are administered in unit dosage form.

Oral administration can be effected utilizing solid and liquid dosage unit forms such as powders, tablets, capsules, granules and the like.

Powders are prepared by comminuting the compound to a suitable fine size and mixing with a similarly comminuted pharmaceutical carrier such as an edible carbohydrate as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder as carboxymethyl cellulose, an alginate, gelatin, or polyvinyl pyrrolidone, a solution retardant such as paraffin, a resorption accelerator such as a quarternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds and pharmaceutically accetable acid addition salts of the present invention can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations or oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example flavored aqueous solution, while elixirs are prepared through myristyl palmitate or mixtures thereof.

In determining the dosage to be administered a number of factors such as the age of the patient, body weight, severity of condition, administration route, and the like must be considered. Generally, from about 1 to 100 mg per day of a compound of the present invention should be administered to an average human adult preferably from 1 to 10 mg per day for an average human adult. It is preferred that the administration be subdivided so that administration takes place 2 or 3 times per day.

REFERENCE EXAMPLE A (methyl α,α-(2.2'-dithienyl)glycolate)

A Grignard reagent, prepared from 0.73 g magnesium and 4.9 g 2-bromothiophene in anhydrous tetrahydrofuran (THF) in the usual way, was added dropwise under a nitrogen gas stream to a solution of 4.25 g methyl α-oxo-2-thiopheneacetate in anhydrous THF under ice cooling, and stirring was continued for two hours under colling with water. A solution of 1.5 g ammonium chloride in 15 ml water was then added under ice cooling. The separated organic layer was collected, dried over anhydrous magnesium sulfate and concentrated under reduced pressure, leaving crystals of the objective compound. Recrystallization from a mixture of n-hexane and diethyl ether gave 3.5 g of pure crystals.

M.p.: 92–93° C.

REFERENCE EXAMPLE B (1.1-dimethyl-2-propynyl α-cyclohexyl-α-phenylglycolate)

A Grignard reagent, prepared from 3.38 g magnesium and 2.27 g cyclohexyl bromide in anhydrous THF in the usual way, was added dropwise under a nitrogen gas stream to a solution of 1,1-dimethyl-2-propynyl benzoylformate in anyhdrous THF under ice cooling, and stirring was continued for 18 hours under cooling with water. A solution of 7.5 g ammonium chloride in 30 ml water was then added under ice cooling. The separated organic layer was collected, washed with water, dried over anhydrous magnesium sulfate and concentrated under reduced pressure. The oily residue was purified by silica gel column chromatography (Wako Gel C-200; 1:15 mixture of ethyl acetate and n-hexane), giving 17.6 g of the objective compound as oil.

IR (film, cm$^{-1}$): 3500, 3300, 2920, 2110, 1725, 1120.

The following compounds were obtained in an analogous manner:

1,1-dimethyl-2-propynyl α-cyclopentyl-α-phenylglycolate.

IR (film, cm$^{-1}$): 3500, 2950, 1725, 1250, 1130, 695

1,1-dimethyl-2-propynyl α-phenyl-α-(2-thienyl)glycolate.

IR (film, cm⁻¹): 3480, 1730, 1255, 1125, 695 1,1-dimethyl-2-propynyl α,α-diphenylglycolate.

IR (film, cm⁻¹): 3500, 3295, 2110, 1725, 1125 1-methyl-2-propynyl α-cyclohexyl-α-(2-thienyl)glycolate.

IR (film, cm⁻¹): 3500, 3300, 2940, 2110, 1725 1-methyl-2-propynyl α-cyclopentyl-α-(2-thienyl)glycolate.
Elemental analysis ($C_{15}H_{18}O_3S.1/10H_2O$):
Calcd. (%) C 64.30, H 6.54.
Found (%) C 64.03, H 6.63.
1,1-dimethyl-2-propynyl α-cyclohexyl-α-(2-thienyl)-glycolate.

IR (film, Cm⁻¹): 3500, 3300, 2910, 2100, 1725, 1120 1,1-dimethyl-2-propynyl α-cyclopentyl-α-(2-thienyl)-glycolate.

IR (film, cm⁻¹): 3500, 3300, 2950, 2110, 1725, 1125
1-ethynyl-I-cyclopentyl α-cyclohexyl-α-phenylglycolate
1-ethynyl-1-cyclopentyl α-cyclopentyl-α-phenylglycolate
1-ethynyl-1-cyclohexyl α-cyclohexyl-α-phenylglycolate
1-ethynyl-1-cyclohexyl α-cyclopentyl-α-phenylglycolate
1-ethynyl-1-cyclopentyl α-phenyl-α-(2-thienyl)glycolate
1-ethynyl-1-cyclohexyl α-phenyl-α-(2-thienyl)glycolate
N-(2-propynyl)-2-hydroxy-2,2-(2,2,-dithienyl)acetamide
M.p.: 128° C.
N-(2-propynyl)-2-cyclopentyl-2-hydroxy-2-(2-thienyl)acetamide
IR (film, cm⁻¹): 3390, 3300, 2300, 1665, 1515
N-(2-propynyl)-2-cyclohexyl-2-hydroxy-2-(2-thienyl)acetamide
M.p.: 134–135° C.
N-(2-propynyl)-2-cyclohexyl-2-hydroxy-2-phenylacetamide
M.p. 142.5–143° C.

REFERENCE EXAMPLE C (4-diethylamino-1-methyl-2-butynyl α-oxo-2-thiopheneacetate To a solution of 4.3 g α-oxo-2-thiopheneacetic acid in dichloromethane was added 0.5 ml pyridine, and 6.75 g thionyl chloride was then added dropwise under ice cooling. The mixture was heated under reflux for seven hours and concentrated under reduced pressure, diethyl ether was added to the residue, the insoluble matters were filtered off, and the filtrate was concentrated under reduced pressure. The oily substance thus obtained (4.1 g) was added dropwise to an etheral solution of 4.5 g 5-diethylamino-3-pentyn-2-ol under ice cooling, and the mixture was stirred for 18 hours under cooling with water and basified with an aqueous solution of potassium carbonate. The separated etheral layer was collected, washed with water, dried over anhydrous magnesium sulfate and concentrated under reduced pressure. The oily residue was purified by silica gel column chromatography (Wako Gel C-200; ethyl acetate), giving 2.48 g of the objective compound as oil.

IR (film, Cm⁻¹): 1735, 1665, 1410, 1195

The following compound was prepared in an analogous manner:
4-diethylamino-2-butynyl α-oxo-2-thiopheneacetate.

IR (film cm⁻¹): 1735, 1660, 1410, 1185.

REFERENCE EXAMPLE D (N-(4-diethylamino-2-butynyl)benzoylformamide)

N-(2-propynyl)benzoylformamide (0.36 g), 80% paraformaldehyde (90 mg) and diethylamine (162 mg) were added to anhydrous dioxane, 4 mg cuprous chloride was further added, and the mixture was heated at 70 to 80° C. for 1.5 hours with stirring. After cooling to room temperature, the reaction mixture was acidified with 5% hydrochloric acid. The separated aqueous layer was collected and washed with diethyl ether, 5% aqueous solution of caustic soda was added under ice cooling to make the solution weakly alkaline, and the alkaline solution was extracted with diethyl ether. The etheral extract was washed with water, dried over anhydrous magnesium sulfate and concentrated under reduced pressure. The oily residue thus obtained was purified by silica gel column chromatography (Wako Gel C-200; chloroform), giving 0.39 g of the objective compound.

IR: 3300, 1690, 1665, 1215

REFERENCE EXAMPLE E (4-bromo-1,1-dimethyl-2-butynyl α-cyclohexyl-α-phenylglycolate To a solution of 9.5 g 4-diethylamino-1,1-dimethyl-2-butynyl α-cyclohexyl-α-phenylglycolate in diethyl ether, was added dropwise an etheral solution of 3.2 g cyanogen bromide, and the mixture was stirred for one hour under ice cooling and then for 18 hours under cooling with water. 2N-HCl (14 ml) was added to the reaction mixture under ice cooling, and the separated etheral layer was collected, washed with water, dried over anhydrous magnesium sulfate and concentrated under reduced pressure. The residue left was purified by silica gel column chromatography (Wako Gel C-200; 1:15 mixture of ethyl acetate and n-hexane), giving 6.0 g of the objective compound as colorless oil.

IR (film, cm⁻¹) 3500, 2920, 1725, 1270, 1250, 1235, 1120

EXAMPLE 1

(4-diethylamino-2-butynyl α,α-(2,2'-dithienyl)-glycolate hydrochloride)

To a suspension of 37 mg newly prepared sodium methoxide in n-heptane, were added 1.09 g 4-diethylamino-2-butynol and 1.78 g methyl α,α-(2,2,-dithienyl)glycolate, and the mixture was heated under reflux for six hours while removing the formed methanol through a dehydration tube. Ice and ethyl acetate were added to the reaction mixture in that order, the separated organic layer was collected, washed thrice with water and dried over anhydrous sodium sulfate, and the solvents were distilled off from the dried solution, leaving 2.6 g of dark-red oil. It was purified by column chromatography (silica gel 30 g; 100:1 to 10:1 mixtures of chloroform and methanol), giving 1.6 g of the objective compound as dark-red oil. It was dissolved in diethyl ether and coverted to hydrochloride by addition of etheral solution of hydrogen chloride, which was recrystallized from a mixture of ethanol and diethyl ether, giving 1.18 g of the hydrochloride of objective compound as faint-yellow powder.

M.p.: 138.5–140° C.

Elemental analysis ($C_{18}H_{21}NO_3S_2.HCl$):
Calcd. (%) C 54.05, H 5.54 N 3.50.

EXAMPLE 2

(4-[4-(2-methoxyphenyl-1-piperazinyl]-2-butynyl α,α-(2.2'-dithienyl)glycolate)

Sodium methoxide (54 mg) prepared from 22 mg sodium and anhydrous methanol, 1.6 g methyl α,α-(2,2'-dithienyl)glycolate and 2.1 g 4-[4-(2-methoxyphenyl)-1-piperazinyl]-2-butynyl acetate were added to n-heptane, and the mixture was heated under reflux for 18 hours while removing the formed methyl acetate through a dehydration tube. Ice water was added to the reaction mixture, the separated organic layer was collected and extracted with 10% hydrochloric acid, and the acidic aqueous extract was washed with diethyl ether, basified with 10% aqueous solution of caustic soda and extracted with diethyl ether. The ethereal extract was washed with water, dried over anhydrous magnesium sulfate and concentrated under reduced pressure, and the residue was purified by flash column chromatography (Kieselgel 60H). The oily product thus obtained crystallized when allowed to stand. Recrystallization from a mixture of ethyl acetate and n-hexane gave 0.49 g of the objective compound as white powder.

M.p.: 113–114° C.
Elemental analysis ($C_{25}H_{26}N_2O_4S_2$):
Calcd. (%) C 62.22, H 5.43, N 5.80.
Found (%) C 62.27, H 5.55, N 5.7.

EXAMPLE 3

(4-diethylamino-1-methyl-2-butynyl α,α-(2,2'-dithienyl)glycolate)

A solution of Grignard reagent in anhydrous diethyl ether prepared from 1.5 g 2-bromothiophene and 223 mg magnesium in the usual way was added dropwise to a solution of 4diethylamino-1-methyl-2-butynyl α-oxo-2-thiopheneacetate in anhydrous diethyl ether at −10 to −15° C. under a nitrogen gas stream, and the mixture was stirred at that temperature for three hours. A solution of 492 mg ammonium chloride in 6 ml water was then added at that temperature, and the separated ethereal layer was collected. The aqueous layer was extracted with diethyl ether, the extract was joined to the above ethereal layer, the combined solution was washed with water and dried over anhydrous magnesium sulfate, and the solvent was distilled off from the dried solution under reduced pressure. The residue was subjected to flash column chromatography (Kieselgel 60H; 20:1 mixture of chloroform and methanol), followed by development with a 100:1 mixture of chloroform and methanol. The product thus obtained was recrystallized from a mixture of petroleum ether and diethyl ether, giving 1.47 g of the objective compound as white powder.

M.p.: 65.5–66° C.
Elemental analysis ($C_{19}H_{23}NO_3S_2$)
Calcd. (%) C 60.45, H 6.14, N 3.71.
Found (%) C 60.20, H 6.10, N 3.98.

EXAMPLE 4

(4-diethylamino-1.1-dimethyl-2-butynyl α-cyclohexyla-phenylglycolate hydrochloride)

1,1-dimethyl-2-propynyl α-cyclohexyl-α-phenylglycolate (9.4 g), 90% paraformaldehyde (2.1 g) and cuprous chloride (62 mg) were added to 40 ml anhydrous dioxane, and the mixture was heated on an oil bath of 60° C. with stirring. A solution of 2.5 g diethylamine in 10 ml anhydrous dioxane was then added dropwise over a period of 45 minutes, and stirring was continued for four hours at that temperature. After cooling to room temperature, the insoluble matters were filtered off from the reaction mixture, and the filtrate was concentrated under reduced pressure. The residue left was dissolved in isopropyl ether, 18 ml of 2N-HCl was added to the solution, and the crystals which separated out were collected by filtration and thoroughly washed with isopropyl ether. The hydrochloride thus obtained was dissolved in chloroform, and the solution was washed with ice water, basified with saturated aqueous solution of sodium bicarbonate, again washed with water and dried over anhydrous magnesium sulfate. The dried solution was concentrated under reduced pressure, and the oily substance left was purified by flash column chromatography (Kieselgel 60H; 4:6 mixture of ethyl acetate and n-hexane), giving the objective compound. It was dissolved in diethyl ether and converted to hydrochloride by addition of 15% etheral solution of hydrogen chloride under ice cooling, which was recrystallized from ethyl acetate, giving 9.0 g of pure hydrochloride as colorless prisms.

M.p.: 158–160° C.
Elemental analysis ($C_{24}H_{35}NO_3 \cdot HCl$):
Calcd. (%) C 68.31, H 8.60, N 3.32.
Found (%) C 68.19, H 8.78, N 3.31.

EXAMPLE 5

(4-diethylamino-2-butynyl α-cyclohexyl-α-(2-thienyl)glycolate hydrochloride)

2-propynyl α-cyclohexyl-α-(2-thienyl)glycolate (840 mg), 80% paraformaldehyde (136 mg), diethylamine (265 mg) and cuprous chloride (17 mg) were added to anhydrous dioxane, and the mixture was heated at 80° C. for one hour with stirring. After cooling to room temperature, dioxane was distilled off from the reaction mixture under reduced pressure, water was added to the residue, and the resulting mixture was extracted with chloroform. The extract was washed with water, dried over anhydrous magnesium sulfate and concentrated under reduced pressure. The residue was purified by silica gel column chromatography (Wako Gel C-200; chloroform:methanol/50:1) giving the objective compound as oil. It was converted to hydrochloride by addition of etheral solution of hydrogen chloride, which was recrystallized from a mixture of ethanol, diethyl ether and n-hexane, giving 0.443 g of pure hydrochloride as colorless powder.

M.p.: 119.5° C. (dec.)
Elemental analysis ($C_{20}H_{29}NO_3S \cdot HCl$):
Calcd. (%) C 60.06, H 7.56, N 3.50.
Found (%) C 59.76, H 7.76, N 3.67.

EXAMPLE 6

(N-(4-N',N'-diethylamino-2-butynyl)-2-cyclohexyl-2-hydroxy-2-phenylacetamide)

A Grignard reagent, prepared from 510 mg magnesium and 2.5 g cyclohexyl chloride in anhydrous THF in the usual way, was added dropwise under a nitrogen gas stream to a solution of 2.5 g N-(4-N',N'-diethylamino-2-butynyl)benzoylformate in anhydrous THF under ice cooling, and stirring was continued at room temperature for 18 hours. A solution of 1.12 g ammonium chloride in 15 ml water was then added under ice cooling. The separated organic layer was collected, washed with water, dried over anhydrous magnesium sulfate and concentrated under reduced pressure, and the residue was purified by flash column chromatography (Kieselgel 60H). The oily product thus obtained crystallized when allowed to stand. Recrystallization from a mixture of diethyl ether and petroleum ether gave 0.74 g of pure product as white powder.

M.p.: 105–105.5° C.
Elemental analysis ($C_{22}H_{32}N_2O_2$):
Calcd. (%) C 74.12, H 9 05, N 7.86.
Found (%) C 74.18, H 9.12, N 7.75.

EXAMPLE 7

(1,1-dimethyl-4-(1-pyrrolidinyl)-2-butynyl α-cyclopentyl-α-phenylglycolate hydrochloride)

A solution of 90% paraformaldehyde (243 mg) and pyrrolidine (440 mg) in anhydrous dioxane was heated at 80° C. for one hour with stirring, 1.6 g 1,1-dimethyl-2-propynyl α-cyclopentyl-α-phenylglycolate was then added, and the mixture was heated at 100° C. for 18 hours. The reaction mixture was concentrated under reduced pressure, the residue was dissolved in isopropyl ether, and the solution was washed with water and extracted with 5% hydrochloric acid. The acidic aqueous extract was washed with diethyl ether and extracted with chloroform, and the extract was washed with ice water and treated with saturated aqueous solution of sodium bicarbonate. The separated organic layer was collected, washed with water, dried over anhydrous magnesium sulfate and concentrated under reduced pressure, and the oily residue was purified by flash column chromatography (Kieselgel 60H; a mixture of 40% ethyl acetate and n-hexane). The oily product thus obtained was converted to hydrochloride by addition of 20% ethereal solution of hydrogen chloride, which was recrystallized from a mixture of ethyl acetate and acetone, giving 1.37 of pure hydrochloride as colorless rods.

M.p 167–168° C.
Elemental analysis ($C_{23}H_{31}NO_3.HCl$):
Calcd. (%) C 68.05, H 7.95, N 3.45.
Found (%) C 67.84, H 7.93, N 3.36.

EXAMPLE 8

(4-ethylamino-1,1-dimethyl-2-butynyl α-cyclohexyl-α-phenylglycolate hydrochloride)

A solution of 6.0 g 4-bromo-1,1-dimethyl-2-butynyl α-cyclohexyl-α-phenylglycolate in benzene, was added dropwise to a solution of 8.2 g ethylamine in benzene over a period of one hour under ice cooling, and stirring was continued for 18 hours. The reaction mixture was washed with water and then with saturated aqueous solution of sodium chloride, dried over anhydrous magnesium sulfate and concentrated under reduced pressure. The oily residue was purified by column chromatography (Wako Gel C-200; 2:1 mixture of ethyl acetate and n-hexane), and the oily product thus obtained was dissolved in isopropyl ether and converted to hydrochloride by addition of 15% ethereal solution of hydrogen chlordie. Recrystallization from a mixture of ethanol and ethyl acetate gave 3.6 g of pure hydrochloride as colorless prisms.

M.p.: 158–160° C.
Elemental analysis ($C_{22}H_{31}NO_3HCl$):
Calcd. (%) C 67.07, H 8.19, N 3.56.
Found (%) C 66.75, H 8.25, N 3.75.

The following compounds were prepared in the same way as above:

EXAMPLE 9

(4-(1-pyrrolidinyl)-2-butynyl α,α-(2,2'-dithienyl)glycolate

M.p.: 128–129° C.
Elemental analysis ($C_{18}H_{19}NO_3S_2$):
Calcd. (%) C 59.81, H 5.30, N 3.87.
Found (%) C 59.84, H 5.41, N 3.94.

EXAMPLE 10

(4-morpholino-2-butynyl α,α-(2,2'-dithienyl)glycolate

M.p.: 113–115° C.
Elemental analysis ($C_{18}H_{19}NO_4S_2$):
Calcd. (%) C 57.27, H 5.07, N 3.71.
Found (%) C 57.07, H 5.29, N 3.71.

EXAMPLE 11

(4-piperidino-2-butynyl α,α-(2,2'-dithienyl)glycolate

M.p.: 140–141° C.
Elemental analysis ($C_{19}H_{21}NO_3S_2$):
Calcd. (%) C 60.77, H 5.64, N 3.73.
Found (%) C 61.07, H 5.96, N 3.70.

EXAMPLE 12

M.p.: 106–107° C.
Elemental analysis ($C_{19}H_{21}NO_3S_2$):
Calcd. (%) C 60.77, H 5.64, N 3.73.
Found (%) C 60.70, H 5.78, N 3.75.

EXAMPLE 13

(4-diethylamino-1-methyl-2-butynyl α-cyclohexyl-α-(2-thienyl)glycolate hydrochloride)

M.p.: 156–159° C. (dec.)
Elemental analysis ($C_{21}H_{31}NO_3S.HCl.3/4H_2O$):
Calcd. (%) C 58.99, H 7.89, N 3.28.
Found (%) C 59.17, H 7.85, N 3.44.

EXAMPLE 14

(4-diethylamino-1,1-dimethyl-2-butynyl α-cyclohexyl-α-(2-thienyl)glycolate hydrochloride)

M.p.: 191–192° C.
Elemental analysis ($C_{22}H_{33}NO_3S.HCl$):
Calcd. (%) C 61.73, H 8.01, N 3.27.
Found (%) C 61.51, H 7.99, N 3.33.

EXAMPLE 15

(1,1-dimethyl-4-(1-pyrrolidinyl)-2-butynyl α-cyclohexyl-α-(2-thienyl)glycolate hydrochloride)

M.p.: 164–165° C.
Elemental analysis ($C_{22}H_{31}NO_3S.HCl$):
Calcd. (%) C 62.03, H 7.57, N 3.29.
Found (%) C 61.92, H 7.56, N 3.29.

EXAMPLE 16

(4-diethylamino-2-butynyl α-cyclopentyl -α-(2-thienyl)glycolate)

M.p.: 55–57° C.
Elemental analysis ($C_{19}H_{27}NO_3S$):
Calcd. (%) C 65.30, H 7.79, N 4.01.
Found (%) C 65.20, H 8.07, N 4.12.

EXAMPLE 17

(4-diethylamino-1.1-dimethyl-2-butynyl α-cyclopentyl-α-(2-thienyl)glycolate hydrochloride)

M.p.: 155–156° C.
Elemental analysis ($C_{21}H_{31}NO_3S.HCl.1/4H_2O$):
Calcd. (%) C 60.26, H 7.82, N 3.34.
Found (%) C 60.38, H 7.86, N 3.60.

EXAMPLE 18

(4-N′,N′-diethylamino-2-butynyl)-2-hydroxy-2,2-(2,2′-dithienyl)acetamide)

M.p.: 98–100° C.
Elemental analysis ($C_{18}H_2N_2O_2S_2$):
Calcd. (%) C 59.64, H 6.12, N 7.73.
Found (%) C 59.58, H 6.14, N 7.59.

EXAMPLE 19

(N-(4-N′,N′-diethylamino-2-butynyl)-2-cyclohexyl-2-hydroxy-2-(2-thienyl)acetamide)

M.p.: 77–78° C.
Elemental analysis ($C_{20}H_{30}N_2O_2S$):
M.p.: 77–78° C.
Elemental analysis ($C_{20}H_{30}N_2O_2S$):
Calcd. (%) C 66.26, H 8.34, N 7.73.
Found (%) C 66.12, H 8.59, N 7.65.

EXAMPLE 20

(N-(4-N′,N′-diethylamino-2-butynyl)-2-cyclopentyl-2-hydroxy -2 -(2-thienyl)acetamide hydrochloride)

M.p.: 131–132° C.
Elemental analysis ($C_{19}H_{28}N_2O_2S.HCl$):
Calcd. (%) C 59.28, H 7.59, N 7.28.
Found (%) C 59.03, H 7.74, N 7.33.

EXAMPLE 21

(N-(4-pyrrolidino-2-butynyl)-2-hydroxy-2,2-(2,2′-dithienyl)acetamide)

M.p.: 164–166° C.
Elemental analysis ($C_{18}H_{20}N_2O_2S_2$):
Calcd. (%) C 59.97, H 5.59, N 7.77.
Found (%) C 59.72, H 5.87, N 7.70.

EXAMPLE 22

(N-(4-pyrrolidino-2-butynyl)-2-cyclohexyl-2-hydroxy-2-phenylacetamide)

M.p.: 112–114° C.
Elemental analysis ($C_{22}H_{30}N_2O_2$):
Calcd. (%) C 74.54, H 8.53, N 7.90.
Found (%) C 74.16, H 8.68, N 7.84.

EXAMPLE 23

(4-diethylamino-1-methyl-2-butynyl α-cyclohexyl-α-phenylglycolate hydrochloride)

M.p.: 80–82° C.
Elemental analysis ($C_{23}H_{33}NO_3.HCl.\frac{1}{2}H_2O$):
Calcd. (%) C 64.17, H 8.54, N 3.25.
Found (%) C 64.39, H 8.46, N 3.31.

EXAMPLE 24

(1,1-dimethyl-4-(1-pyrrolidinyl)-2-butynyl α-cyclohexyl-α-phenylglycolate hydrochloride)

M.p.: 174–175° C.
Elemental analysis ($C_{24}H_{33}NO_3.HCl$):
Calcd. (%) C 68.64, H 8.16, N 3.33.
Found (%) C 68.40, H 8.04, N 3.26.

EXAMPLE 25

(1,1-dimethyl-4-dimethylamino-2-butynyl α-cyclohexyl-α-phenylglycolate hydrochloride)

M.p.: 155–159° C.
Elemental analysis ($C_{22}H_{31}NO_3.HCl.\frac{1}{2}H_2O$):
Calcd. (%) C 65.57, H 8.25, N 3.48.
Found (%) C 65.44, H 8.32, N 3.50.

EXAMPLE 26

(1,1-dimethyl-4-morpholino-2-butynyl α-cyclohexyl-α-phenylglycolate hydrochloride)

M.p.: 186–190° C.
Elemental analysis ($C_{24}H_{33}NO_3.HCl$):
Calcd. (%) C 66.12, H 7.86, N 3.21.
Found (%) C 65.91, H 7.94, N 3.22.

EXAMPLE 27

(1,1-dimethyl-4-piperidino-2-butynyl α-cyclohexyl-α-phenylglycolate hydrochloride)

M.p.: 207–208° C.
Elemental analysis ($C_{25}H_{35}NO_3.HCl$):
Calcd. (%) C 68.79, H 8.44, N 3.31.
Found (%) C 69.18, H 8.36, N 3.23.

EXAMPLE 28

(4-diethylamino-1,1-dimethyl-2-butynyl α-cyclopentyl-α-phenylglycolate hydrochloride)

M.p.: 120–121° C.
Elemental analysis ($C_{23}H_{33}NO_3.HCl.\frac{1}{4}H_2O$):
Calcd. (%) C 66.97, H 8.43, N 3.40.
Found (%) C 67.08, H 8.39, N 3.40.

EXAMPLE 29

(1,1-dimethyl-4-piperidino-2-butynyl α-cyclopentyl-α-phenylglycolate hydrochloride)

M.p. 157–158° C.
Elemental analysis ($C_{24}H_{33}NO_3.HCl.\frac{1}{4}H_2O$):
Calcd. (%) C 67.91, H 8.19, N 3.30.
Found (%) C 67.90, H 8.38, N 3.21.

EXAMPLE 30

(1,1-dimethyl-4-dimethylamino-2-butynyl α-cyclopentyl-α-phenylglycolate hydrochloride)

M.p.: 125–127° C.
Elemental analysis ($C_{21}H_{29}NO_3.HCl.\frac{1}{2}H_2O$):
Calcd. (%) C 64.85, H 8.03, N 3.60.
Found (%) C 65.01, H 8.20, N 3.62.

EXAMPLE 31

(1,1-dimethyl-4-morpholino-2-butynyl α-cyclopentyl-α-phenyloglycolate hydrochloride)

M.p.: 150–151° C.
Elemental analysis ($C_{23}H_{31}NO_4.HCl.\frac{1}{4}H_2O$):
Calcd. (%) C 64.78, H 7.68, N 3.28.
Found (%) C 65.07, H 7.75, N 3.27.

EXAMPLE 32

(1-(3-diethylamino-1-propynyl)cyclopentyl α-cyclopentyl-α-phenylglycolate hydrochloride)

M.p.: 132–133° C.
Elemental analysis ($C_{25}H_{35}NO_3.HCl.\frac{1}{4}H_2O$):

Calcd. (%) C 68.47, H 8.39, N 3.10.
Found (%) C 68.56, H 8.42, N 3.27.

EXAMPLE 33

(1-(3-diethylamino-1-propynyl)cyclohexyl α-cyclopentyl-α-phenylglycolate hydrochloride)

M.p.: 113–115° C.
Elemental analysis ($C_{26}H_{37}NO_3 \cdot HCl \cdot \frac{1}{4}H_2O$):
Calcd. (%) C 69.00, H 8.57, N 3.10.
Found (%) C 69.14, H 8.65, N 3.14.

EXAMPLE 34

(4-diethylamino-1,1-dimethyl-2-butynyl α-phenyl-α-(2-thienyl)glycolate hydrochloride)

M.p.: 155–156° C.
Elemental analysis ($C_{22}H_{27}NO_3 \cdot HCl$):
Calcd. (%) C 62.62, H 6.69, N 3.32.
Found (%) C 62.4, H 6.78, N 3.37.

EXAMPLE 35

(1,1-dimethyl-4-(1-pyrrolidinyl)-2-butynyl α-phenyl-α-(2-thienyl)glycolate hydrochloride)

M.p.: 129–130° C.
Elemental analysis ($C_{22}H_{25}NO_3S \cdot HCl \cdot 1/5H_2O$):
Calcd. (%) C 62.38, H 6.04, N 3.30.
Found (%) C 62.48, H 6.12, N 3.35.

EXAMPLE 36

(1-(3-diethylamino-1-propynyl)cyclopentyl α-phenyl-α-(2-thienyl) glycolate hydrochloride)

M.p.: 149–151° C.
Elemental analysis ($C_{24}H_{29}NO_3S \cdot HCl$):
Calcd. (%) C 64.34, H 6.75, N 3.13.
Found (%) C 64.09, H 6.57, N 3.18.

EXAMPLE 37

(1-[3-(1-pyrrolidinyl)-1-propynyl]cyclopentyl α-phenyl-α-(2thienyl) glycolate hydrochloride)

M.p. 133–135° C.
Elemental analysis ($C_{24}H_{27}NO_3S \cdot HCl$):
Calcd (%) C 64.63, H 6.33, N 3.14.
Found (%) C 64.35, H 6.57, N 3.18.

EXAMPLE 38

(1-(3-diethylamino-1-propynyl)cyclohexyl α-phenyl-α-(2-thienyl)glycolate hydrochloride)

M.p.: 120–121° C.
Elemental analysis ($C_{25}H_{31}NO_3S \cdot HCl$):
Calcd. (%) C 64.99, H 6.98, N 3.03.
Found (%) C 64.99, H 6.93, N 3.00.

EXAMPLE 39

(4-diethylamino-1,1-dimethyl-2-butynyl α,α-diphenylglycolate hydrochloride)

M.p.: 176–177° C.
Elemental analysis ($C_{24}H_{29}NO_3 \cdot HCl$):
Calcd. (%) C 69.30, H 7.27, N 3.37.
Found (%) C 69.09, H 7.43, N 3.44.

EXAMPLE 40

(1,1-dimethyl-4-(1-pyrrolidinyl)-2-butynyl α,α-diphenylglycolate hydrochloride)

M.p.: 144–146° C.
Elemental analysis ($C_{24}H_{27}NO_3 \cdot HCl \cdot 1/10H_2O$):
Calcd (%) C 69.34, H 6.84, N 3.37.
Found (%) C 69.07, H 6.81, N 3.42.

EXAMPLE 41

(1-(3-diethylamino-1-propynyl)cyclohexyl α-cyclohexyl-α-phenylglycolate hydrochloride)

M.p.: 132–134° C.
Elemental analysis ($C_{27}H_{39}NO_3 \cdot HCl \cdot \frac{1}{4}H_2O$):
Calcd. (%) C 69.50, H 8.75, N 3.00.
Found (%) C 69.47, H 8.69, N 3.13.

EXAMPLE 42

(1-(3-diethylamino-1-propynyl)cyclohexyl α-cyclohexyl-α-phenylglycolate hydrochloride)

M.p.: 172–173° C.
Elemental analysis ($C_{26}H_{37}NO_3 \cdot HCl$):
Calcd. (%) C 69.70, H 8.55, N 3.13.
Found (%) C 69.56, H 8.62, N 3.09.

TEST EXAMPLE

The result of pharmacological tests illustrating the efficacy of a typical example of the compounds of the present invention is set forth below.

Test Methods

1. Action upon detrusor muscles of excised rabbit bladder

The bladder was extracted from JW/NIBUS/RABITON rabbits (male; 2 to 3 kg) and incised along longitudinal muscles, thus preparing specimens 2 to 3 mm wide and 10 mm long. Each of the specimens was suspended under a load of 1 gr in a Magnus bath filled with Modified Krebs, solution (37±0.1° C.; aerated with mixed gas).

(1) Anticholinergic action

The specimens were contracted by carbachol cumulation, and a reaction curve with respect to carbachol concentration was obtained. Similar experiments were conducted with detrusor muscles of rabbits treated with drugs being tested, and $pA_2$ values were calculated according to the method of Arunlakshana and Shild.

(2) Ca$^{++}$ Antagonism

The solution in Magnus bath was replaced by Ca$^{++}$-free, high KCl-modified Krebs, solution. The specimens were contracted by cumulation of calcium chloride and a reaction curve with respect to calcium chloride concentration was obtained. Similar experiments were conducted with detrusor muscles of rabbits treated with drugs being tested, and pA: values were calculated according to the method of Arunlakshana and Shild.

The result obtained is shown in Table 1. The compound of Example 4 showed weaker anticholinergic action (1/17) and higher Ca$^{++}$ antagonism (8.3 times as high), compared with oxybutynin.

2. Action upon the rhythmic contraction of rat bladder

Urethane-anesthetized SD rats (male; 280 to 360 g) were used as test animals in this test. A small incision was made at the top of each bladder, a baloon was inserted through the cut, warm water of about 37° C. was injected into the baloon at a constant internal pressure, and the urinating contraction of rhythmic amplitude was recorded. When the frequency of contraction reached a constant level, a drug being tested was cumulatively administered (i.v.) to test its effect upon the contraction. The result obtained is summarized in Table 2.

The compound of Example 4 showed dose-dependent action to suppress the frequency of contraction at doses of 0.1 mg/kg (i.v.) and higher, while no such action was observed with oxybutynin.

3. Acute toxicity ddY-Mice (male; 6 to 7 week age) were used as test animals (each group consisting of four mice). Each of the mice was fasted from the previous day (16 to 18 hours before), a drug being tested was orally administered by using a gastric tube, and $LD_{50}$ value was calculated from the mortality one week later according to the method of Weil.

The $LD_{50}$ value for the compound of Example 4 was 841 mg/kg (p.o.) a far lower toxicity level than that of oxybutynin which has an $LD_{50}$ value of 354 mg/kg (p.o.).

4. Concentration of unchanged drug in the serum

A drug being tested was administered to an SD rat (male; 280 to 360 g) in a dose of 3 mg/kg (i.v.), blood samples were taken out at predetermined intervals, and the change in the concentration of said drug left unchanged in the serum was measured. The half-life period ($t_{\frac{1}{2}}$) of the compound of Example 4 was 0.85 hour (far longer than the value of oxybutynin, 0.28 hour), indicating its longer duration.

TABLE 1

| Action upon Detrusor Muscles of Excised Rabbit Bladder | | |
|---|---|---|
| | pA$_2$ value | |
| | Anticholinergic action | Ca$^{++}$ Antagonism |
| Compd. of Example 4 | 7.33 | 6.72 |
| Oxybutynin | 8.56 | 5.80 |

TABLE 2

| | Action upon Rhythmic Contraction of Rat Bladder | | | | |
|---|---|---|---|---|---|
| | Before | Frequency (cycles of contraction per minute) (0 to 15 minutes) | | | |
| Drugs | administration | 0.1 mg/kg (i.v.) | 0.3 mg/kg (i.v.) | 1.0 mg/kg (i.v.) | 3.0 mg/kg (i.v.) |
| Compd. of Example 4 | 1.3 ± 0.3 | 1.1 ± 0.3 | 0.8 ± 0.2 | 0.3 ± 0.1* | 0.0 ± 0.0** |
| Oxybutynin | 1.0 ± 0.1 | 1.1 ± 0.2 | 1.0 ± 0.2 | 1.2 ± 0.1 | 1.2 ± 0.2 |

*p < 0.05
**p < 0.01

From the foregoing, the compounds of the present invention show weaker anticholinergic action and stronger antagonism against calcium as compared with oxybutynin, and hence are characterized by an ideal balance between the two actions, thereby exhibiting excellent therapeutical effects against pollakiuria and other hyperactive bladder as well as various urinary incontinence. In addition, the half-life period in the serum is very long, indicating long duration, and the toxicity is also very low.

As a result of the excellent action, long duration and low toxicity of the compounds of the present invention not observed with known drugs, the compounds of this invention can be used as drugs of high safety for treating pollakiuria and other hyperactive bladder conditions as well as various urinary incontinences caused by neurogenic bladder, bladder contracture, nervous cystitis and enuresis which require long-term administration.

What is claimed is:

1. A compound of the formula (I):

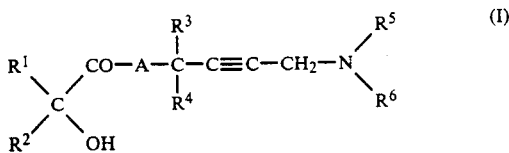

or a pharmaceutically acceptable acid addition salt thereof, wherein $R^1$ and $R^2$ are the same or different and each is cycloalkyl of 5 to 7 carbon atoms, phenyl or 2-thienyl; $R^3$ and $R^4$ are the same or different and each is hydrogen or straight or branch chain lower alkyl, or $R^3$ an $R^4$ together with the carbon atom to which they are attached are cycloalkyl of 5 to 6 carbon atoms; $R^5$ and $R^6$ are the same or different and each is hydrogen or straight or branch chain lower alkyl and A is O; provided that when either $R^1$ and $R^2$ is phenyl, $R^3$ and $R^4$ are not both hydrogen.

2. A compound according to claim 1 wherein $R^3$ and $R^4$ are the same or different and each is hydrogen or straight or branch chain alkyl of 1 to 4 carbon atoms.

3. A compound according to claim 1 wherein $R^3$ and $R^4$ together with the carbon atom to which they are attached are cycloalkyl of 5 to 6 carbon atoms.

4. A compound according to claim 1 wherein $R^5$ and $R^6$ are the same or different and each is hydrogen or straight or branch chain alkyl or 1 to 4 carbon atoms.

5. A compound according to claim 1 in the form of an acid addition salt selected from the group consisting of the hydrochloride, sulphate, nitrate, phosphate, oxalate, tartrate, maleate and benzenesulfonate.

6. A pharmaceutical composition useful for treating pollakiuria and incontinence in humans and animals which comprises a therapeutically effective amount of a compound of the formula (I):

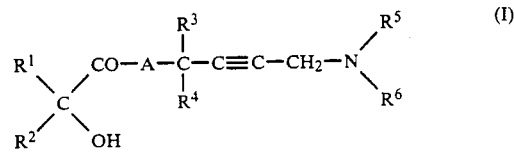

or a pharmaceutically acceptable acid addition salt thereof, wherein $R^1$ and $R^2$ are the same or different and each is cycloalkyl of 5 to 7 carbon atoms, phenyl or 2-thienyl; $R^3$ and $R^4$ are the same or different and each is hydrogen or straight or branch chain lower alkyl, or $R^3$ and $R^4$ together with the carbon atom to which they are attached are cycloalkyl of 5 to 6 carbon atoms; $R^5$ and $R^6$ are the same or different and each is hydrogen or straight or branch chain lower alkyl and A is O; provided that when either $R^1$ or $R^2$ is phenyl, $R^3$ and $R^4$ are not both hydrogen in combination with a pharmaceutically acceptable carrier.

7. A composition according to claim 6 wherein $R^3$ and $R^4$ are the same or different and each is hydrogen or straight or branch chain alkyl of 1 to 4 carbon atoms.

8. A composition according to claim 6 wherein $R^3$ and $R^4$ together with the carbon atom to which they are attached are cycloalkyl of 5 to 6 carbon atoms.

9. A composition according to claim 6 wherein $R^3$ and $R^4$ are the same or different and each is hydrogen or straight or branch chain alkyl of 1 to 4 carbon atoms.

10. A composition according to claim 6 wherein the compound is in the form of an acid addition salt selected from the group consisting of the hydrochloride, sulphate, nitrate, phosphate, oxalate, tartrate, maleate and benzenesulfonate.

11. A method of treating pollakiuria and incontinence in humans and animals which comprises administering to a human or animal in need thereof a therapeutically effective amount of a compound of the formula (I):

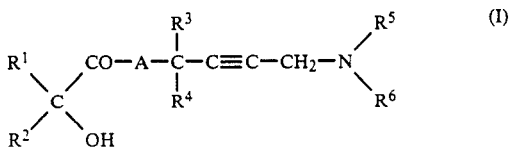

or a pharmaceutically acceptable acid addition salt thereof, wherein $R^1$ and $R^2$ are the same or different and each is cycloakyl of 5 to 7 carbon atoms, phenyl or 2-thienyl; $R^3$ and $R^4$ are the same or different and each is hydrogen or straight or branch chain lower alkyl, or $R^3$ or $R^4$ together with the carbon atom to which they are attached are cycloakyl of 5 to 6 carbon atoms; $R^5$ and $R^6$ are the same or different and each is hydrogen or straight or branch chain lower alkyl and A is O; provided that when either $R^1$ or $R^2$ is phenyl, $R^3$ and $R^4$ are not both hydrogen in combination with a pharmaceutically acceptable carrier.

12. A method according to claim 11 wherein $R^3$ and $R^4$ are the same or different and each is hydrogen or straight or branch chain alkyl of 1 to 4 carbon atoms.

13. A method according to claim 11 wherein $R^3$ and $R^4$ together with the carbon atom to which they are attached are cycloakyl of 5 to 6 carbon atoms.

14. A method according to claim 11 wherein $R^5$ and $R^6$ are the same or different and each is hydrogen or straight or branch chain alkyl of 1 to 4 carbon atoms.

15. A method according to claim 11 wherein the compound is in the form of an acid addition salt selected from the group consisting of the hydrochloride, sulphate, nitrate, phosphate, oxalate, tartrate, maleate and benzenesulfonate.

16. The compound according to claim 1 which is 4-diethylamine-1,1-dimethyl-2-butynyl α-cyclohexyl-α-phenylglycolate hydrochloride.

17. A composition according to claim 6, wherein the compound is 4-diethylamino-1,1-dimethyl-2-butynyl α-cyclohexyl-α-phenylglycolate hydrochloride.

18. A method according to claim 11, wherein the compound is 4-diethylamino-1,1-dimethyl-2-butynyl α-cyclohexyl-α-phenylglycolate hydrochloride.

19. A compound according to claim 1 which is 4-ethylamino-1,1-dimethyl-2-butynyl α-cyclohexyl-α-phenylglycolate hydrochloride.

20. A compound according to claim 6, wherein the compound is 4-ethylamino-1,1-dimethyl-2-butynyl α-cyclohexyl-α-phenylglycolate hydrochloride.

21. A method according to claim 11 wherein the compound is 4-ethylamino-1,1-dimethyl-2-butynyl α-cyclohexyl-α-phenylglycolate hydrochloride.

* * * * *

REEXAMINATION CERTIFICATE (2121st)
United States Patent [19]
Kimura et al.

[11] B1 5,036,098
[45] Certificate Issued    Nov. 2, 1993

[54] BUTYNLAMINE DERIVATIVES AND THEIR PRODUCTION

[75] Inventors: Kiyoshi Kimura, Takatsuki; Masahiro Kise; Iwao Morita, both of Kyoto, all of Japan

[73] Assignee: Nippon Shinyaku Co., Ltd., Japan

Reexamination Request:
No. 90/002,826, Aug. 31, 1992

Reexamination Certificate for:
Patent No.: 5,036,098
Issued: Jul. 30, 1991
Appl. No.: 407,228
Filed: Sep. 14, 1989

[30] Foreign Application Priority Data
Sep. 14, 1988 [JP] Japan .................. 63-231272

[51] Int. Cl.$^5$ ............... C07C 69/732; C07D 333/22; A61K 31/215; A61K 31/38
[52] U.S. Cl. .................... 514/438; 514/444; 514/529; 514/530; 514/534; 544/59; 544/168; 544/171; 544/397; 546/234; 546/239; 548/508; 548/572; 549/59; 549/77; 560/58; 560/118; 564/171; 564/188
[58] Field of Search .............. 560/58, 118; 549/77; 514/438, 529, 530, 534, 444

[56] References Cited
FOREIGN PATENT DOCUMENTS
62-267224 11/1987 Japan .
940540 7/1961 United Kingdom .

OTHER PUBLICATIONS
Acta Pharm. Suecica, vol. 6, (1969), pp. 349–358, R. Dahlbom et al., "Acetylene Compounds of Potential Pharmacological Value".
J. Med. Chem., vol. 8, pp. 719–720, R. Majewski et al., "Anticholinergic Agents. Esters of 4-Dialkyl-(or 4-Polymethylene-)amino-2-butynols", (1965).
Acta Chem. Scand., vol. 17, No. 8, pp. 2354–2356, (1963), (Abstract only), Dahlbom et al.
*Drug Evaluations*, 6th ed., (1986), American Medical Assn., p. 572.

*Primary Examiner*—Emily Bernhardt

[57]     ABSTRACT

Compounds of the formula (I):

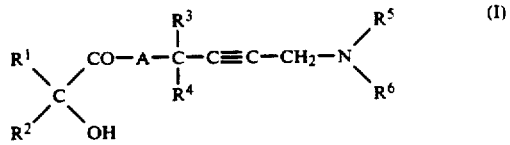

exhibit anti–cholingeric and calcium antagonistic action and are used for treating pollakiuria and incontinence in humans and animals.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 4, 6, 7, 9 and 11-14 are determined to be patentable as amended.

Claims 3, 5, 8, 10 and 15-21, dependent on an amended claim, are determined to be patentable.

1. A compound of the formula (I):

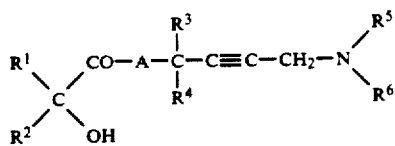

or a pharmaceutically acceptable acid addition salt thereof, wherein *one of* $R^1$ and $R^2$ [are the same or different] *is phenyl* and [each] *the other* is cycloalkyl of 5 to 7 carbon atoms, [phenyl or 2-thienyl] *or $R^1$ and $R^2$ are the same or different and each is cycloalkyl of 5 to 7 carbon atoms or 2-thienyl*; $R^3$ and $R^4$ are the same or different and each is [hydrogen or] straight or branch chain lower alkyl, or $R^3$ and $R^4$ together with the carbon atom to which they are attached are [cycloakyl] *cycloalkyl* of 5 to 6 carbon atoms *or one of $R^3$ and $R^4$ is hydrogen and the other is as above defined*; $R^5$ and $R^6$ are the same or different and each is hydrogen or straight or branch chain lower alkyl and A is O [provided that when either $R^1$ or $R^2$ is phenyl, $R^3$ and $R^4$ are not both hydrogen].

2. A compound according to claim 1 wherein $R^3$ and $R^4$ are the same or different and each is [hydrogen or] straight or branch chain alkyl of 1 to 4 carbon atoms.

4. A compound according to claim 1 wherein *one of* $R^5$ and $R^6$ [are the same or different and each] is hydrogen [or] *and the other is* straight or branch chain alkyl [or] *of* 1 to 4 carbon atoms.

6. A pharmaceutical composition useful for treating pollakiuria and incontinence in humans and animals which comprises a therapeutically effective amount of a compound of formula (I):

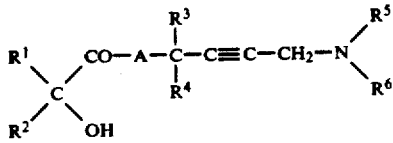

or a pharmaceutically acceptable acid addition salt thereof, wherein *one of* $R^1$ and $R^2$ [are the same or different] *is phenyl* and *the other* is cycloalkyl of 5 to 7 carbon atoms, [phenyl or 2-thienyl] *or $R^1$ and $R^2$ are the same or different and each is cycloalkyl of 5 to 7 carbon atoms or 2-thienyl*; $R^3$ and $R^4$ are the same or different and each is [hydrogen or] straight or branch chain lower alkyl, or $R^3$ and $R^4$ together with the carbon atom to which they are attached are cycloalkyl of 5 to 6 carbon atoms *or one of $R^3$ and $R^4$ is hydrogen and the other is as above defined*; $R^5$ and $R^6$ are the same or different and each is hydrogen or straight or branch chain lower alkyl and A is O [provided that when either $R^1$ or $R^2$ is phenyl, $R^3$ and $R^4$ are not both hydrogen] in combination with a pharmaceutically acceptable carrier.

7. A composition according to claim 6 wherein $R^3$ and $R^4$ are the same or different and each is [hydrogen or] straight or branch chain alkyl of 1 to 4 carbon atoms.

9. A composition according to claim 6 wherein [$R^3$ and $R^4$ are the same or different and each] *one of $R^5$ and $R^6$ is* hydrogen [or] *and the other is* straight or branch chain alkyl of 1 to 4 carbon atoms.

11. A method of treating pollakiuria and incontinence in humans and animals which comprises administering to a human or animal in need thereof a therapeutically effective amount of a compound of the formula (I):

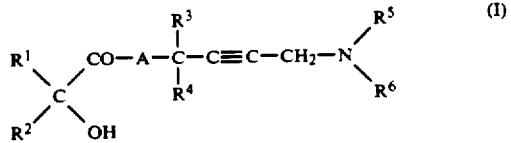

or a pharmaceutically acceptable acid addition salt thereof, wherein *one of* $R^1$ and $R^2$ [are the same or different] *is phenyl* and [each] *the other* is [cycloakyl] *cycloalkyl* of 5 to 7 carbon atoms, [phenyl or 2-thienyl] *or $R^1$ and $R^2$ are the same or different and each is cycloalkyl or 5 to 7 carbon atoms or 2-thienyl*; $R^3$ and $R^4$ are the same or different and each is [hydrogen or] straight or branch chain lower alkyl, or $R^3$ [or] *and $R^4$ together with the carbon atom to which they are attached are* [cycloakyl] *cycloalkyl* of 5 to 6 carbon atoms; *or one of $R^3$ and $R^4$ is hydrogen and the other is as above defined*; $R^5$ and $R^6$ are the same or different and each is hydrogen or straight or branch chain lower alkyl and A is O; [provided that when either $R^1$ and $R^2$ is phenyl, $R^3$ and $R^4$ are not both hydrogen] in combination with a pharmaceutically acceptable carrier.

12. A method according to claim 11 wherein $R^3$ and $R^4$ are the same or different and each is [hydrogen or] straight or branch chain alkyl of 1 to 4 carbon atoms.

13. A method according to claim 11 wherein $R^3$ and $R^4$ together with the carbon atom to which they are attached are [cycloakyl] *cycloalkyl* of 5 to 6 carbon atoms.

14. A method according to claim 11 wherein *one of* $R^5$ and $R^6$ [are the same or different and each] is hydrogen [or] *and the other is* straight or branch chain alkyl of 1 to 4 carbon atoms.

* * * * *